US00RE46830E

(19) United States
(12) Reissued Patent
Droz et al.

(10) Patent Number: US RE46,830 E
(45) Date of Reissued Patent: May 8, 2018

(54) METHOD FOR SOLID PHASE PEPTIDE SYNTHESIS

(71) Applicant: POLYPEPTIDE LABORATORIES HOLDING (PPL) AB, Limhamn (SE)

(72) Inventors: Anne-Sophie Droz, Sierre (CH); Jasmine Schnidrig, Visp (CH); Nicole Studer, Visperterminen (CH); Stéphane Varray, Sierre (CH); Corinne Wenger, Baltschieder (CH); Oleg Werbitzky, Veyras (CH)

(73) Assignee: Polypeptide Laboratories Holding (PPL) AB, Limhamn (SE)

(21) Appl. No.: 14/659,770

(22) Filed: Mar. 17, 2015

Related U.S. Patent Documents

Reissue of:
(64) Patent No.: 7,939,629
Issued: May 10, 2011
Appl. No.: 11/665,541
PCT Filed: Oct. 19, 2005
PCT No.: PCT/EP2005/011226
§ 371 (c)(1),
(2) Date: Apr. 17, 2007
PCT Pub. No.: WO2006/045503
PCT Pub. Date: May 4, 2006

(30) Foreign Application Priority Data

Oct. 19, 2004 (EP) ..... 04024812

(51) Int. Cl.
*C07K 2/00* (2006.01)
*C07K 14/815* (2006.01)

(52) U.S. Cl.
CPC ..... *C07K 14/815* (2013.01)

(58) Field of Classification Search
CPC ..... C07K 14/815
USPC ..... 530/333, 300
See application file for complete search history.

(56) References Cited

U.S. PATENT DOCUMENTS 4,093,610 A 6/1978 Abraham et al.
4,108,846 A 8/1978 Meienhofer
4,169,141 A 9/1979 Topliss et al.
5,166,394 A 11/1992 Breipohl et al.
5,196,404 A 3/1993 Maraganore et al.
5,242,810 A 9/1993 Maraganore et al.
5,362,858 A 11/1994 Bischoff
5,371,184 A 12/1994 Rajagopalan et al.
5,393,873 A 2/1995 Schmied et al.
5,425,936 A 6/1995 Maraganore et al.
5,433,940 A 7/1995 Maraganore et al.
5,443,827 A 8/1995 Haber et al.
5,449,761 A 9/1995 Belinka, Jr. et al.
5,455,181 A 10/1995 Strube et al.
5,516,656 A 5/1996 Misawa et al.
5,541,161 A 7/1996 Krstenansky et al.
5,574,012 A 11/1996 Krstenansky et al.
5,578,288 A 11/1996 Belinka, Jr. et al.
5,593,656 A 1/1997 Belinka, Jr. et al.
5,602,231 A 2/1997 Cotton et al.
5,609,847 A 3/1997 Belinka, Jr. et al.
5,624,822 A 4/1997 Koerwer
5,656,600 A 8/1997 Abelman et al.
5,659,041 A 8/1997 Pollak et al.
5,662,885 A 9/1997 Pollak et al.
5,663,141 A 9/1997 Kurfuerst et al.
5,670,479 A 9/1997 Abelman et al.
5,674,838 A 10/1997 Obermeier et al.
5,681,721 A 10/1997 Steffens et al.
5,681,925 A 10/1997 Broersma, Jr. et al.
5,681,926 A 10/1997 Veber et al.
5,686,564 A 11/1997 Brundish et al.
5,691,311 A 11/1997 Maraganore et al.
5,698,104 A 12/1997 Rhee et al.
5,719,128 A 2/1998 Van Nispen et al.
5,723,576 A 3/1998 De Rosa et al.
5,747,453 A 5/1998 Holladay et al.
5,759,542 A 6/1998 Gurewich
5,767,078 A 6/1998 Johnson et al.
5,767,235 A 6/1998 Nukui et al.
5,780,006 A 7/1998 Pollak et al.
5,786,330 A 7/1998 Fauchere et al.
5,789,540 A 8/1998 Krstenansky et al.
5,817,758 A 10/1998 Lyttle et al.
5,837,808 A 11/1998 Ku et al.
5,880,258 A 3/1999 Muramatsu et al.
5,886,146 A 3/1999 Vlasuk et al.
5,910,481 A 6/1999 Voorberg
5,968,476 A 10/1999 Dean et al.
5,972,648 A 10/1999 Sukesada et al.
5,976,495 A 11/1999 Pollak et al.
5,976,841 A 11/1999 Wnendt et al.

(Continued)

FOREIGN PATENT DOCUMENTS

CA 2120302 3/1994
CA 2496739 3/2004

(Continued)

OTHER PUBLICATIONS

Scatena, Roberto, Bivalirudin, Biogen, Current Opinion in Cardiovascular, Pulmonary & Renal Investigational Drugs, 2(2): 189-194, 2000.*
Albericio et al., Convergent Solid-Phase Peptide Synthesis, Methods in Enzymology, vol. 289, 1997: pp. 313-336.
EMEA Article on Angiox, 2005, pp. 1-32.
Giraud et al.: "A side-reaction in the SPPS of trp-containing peptides," J. Peptide Sci., vol. 5, 1999, pp. 457-461.
Goulas et al., Convergent solid-phase synthesis of hirudin, Journal of Peptide Science, vol. 12, No. 2. 2006, pp. 116-123.
International Preliminary Report on Patentability for PCT/EP2004/014599 completed Apr. 24, 2006.
International Search Report for PCT/EP2004/014599 dated Jul. 15, 2005.

(Continued)

*Primary Examiner* — Johnny F Railey
(74) *Attorney, Agent, or Firm* — Dority & Manning, P.A.

(57) ABSTRACT

A novel method for synthesizing a Hirulog peptide is devised.

42 Claims, No Drawings

(56) References Cited

U.S. PATENT DOCUMENTS

| | | | |
|---|---|---|---|
| 6,005,071 | A | 12/1999 | Krstenansky et al. |
| 6,028,170 | A | 2/2000 | Ku et al. |
| 6,051,418 | A | 4/2000 | Voorberg |
| 6,060,451 | A | 5/2000 | DiMaio et al. |
| 6,127,337 | A | 10/2000 | Konishi et al. |
| 6,133,011 | A | 10/2000 | Wnendt et al. |
| 6,143,719 | A | 11/2000 | Schmaier et al. |
| 6,156,540 | A | 12/2000 | Rosen et al. |
| 6,239,101 | B1 | 5/2001 | Esmon et al. |
| 6,265,204 | B1 | 7/2001 | Ward et al. |
| 6,281,331 | B1 | 8/2001 | Kang et al. |
| 6,313,092 | B1 | 11/2001 | Holladay et al. |
| 6,333,189 | B1 | 12/2001 | Holladay et al. |
| 6,432,921 | B2 | 8/2002 | Adang et al. |
| 6,506,761 | B1 | 1/2003 | Araldi et al. |
| 6,514,730 | B1 | 2/2003 | Schmid et al. |
| 6,544,750 | B1 | 4/2003 | Schmaier et al. |
| 6,579,678 | B1 | 6/2003 | Patten et al. |
| 6,586,182 | B1 | 7/2003 | Patten et al. |
| 6,590,078 | B2 | 7/2003 | Ward et al. |
| 6,703,364 | B2 | 3/2004 | Kalafatis et al. |
| 6,706,512 | B2 | 3/2004 | Gruber et al. |
| 6,710,031 | B2 | 3/2004 | Fukuchi et al. |
| 6,825,168 | B2 | 11/2004 | Cupp et al. |
| 6,875,893 | B2 | 4/2005 | Largeau et al. |
| 6,897,289 | B1 | 5/2005 | Ponsati I Obiols et al. |
| 6,927,279 | B2 | 8/2005 | Cupp et al. |
| 7,060,484 | B1 | 6/2006 | Gibbs et al. |
| 7,074,765 | B2 | 7/2006 | Schmaier et al. |
| 7,074,892 | B2 | 7/2006 | Kalafatis et al. |
| 7,081,447 | B2 | 7/2006 | Thurk |
| 7,084,113 | B2 | 8/2006 | Fukuchi et al. |
| 7,135,534 | B2 | 11/2006 | Kumar et al. |
| 7,138,489 | B2 | 11/2006 | Minamitake et al. |
| 7,144,902 | B1 | 12/2006 | Baucke et al. |
| 7,176,282 | B1 | 2/2007 | Holm et al. |
| 7,348,404 | B2 | 3/2008 | Holm et al. |
| 7,351,771 | B2 | 4/2008 | Barlos et al. |
| 7,407,982 | B2 | 8/2008 | Steinmetzer et al. |
| 7,414,107 | B2 | 8/2008 | Larsen |
| 7,423,021 | B2 | 9/2008 | Thurk et al. |
| 7,425,533 | B2 | 9/2008 | Baker et al. |
| 7,427,260 | B2 | 9/2008 | Pang et al. |
| 7,439,222 | B2 | 10/2008 | Guinn et al. |
| 7,456,152 | B2 | 11/2008 | Ni et al. |
| 7,582,602 | B2 | 9/2009 | Shen |
| 7,582,727 | B1 | 9/2009 | Krishna et al. |
| 7,598,343 | B1 | 10/2009 | Krishna et al. |
| 7,645,858 | B2 | 1/2010 | Stewart |
| 7,691,968 | B2 | 4/2010 | Evans et al. |
| 7,713,928 | B1 | 5/2010 | Palepu et al. |
| 7,795,205 | B2 | 9/2010 | Yu |
| 7,803,762 | B1 | 9/2010 | Palepu et al. |
| 7,824,677 | B2 | 11/2010 | Wong et al. |
| 7,829,659 | B2 | 11/2010 | Grabstein et al. |
| 7,879,792 | B2 | 2/2011 | Schmaier et al. |
| 7,935,786 | B2 | 5/2011 | Larsen |
| 7,985,733 | B1 | 7/2011 | Motheram |
| 8,008,434 | B2 | 8/2011 | Brandt et al. |
| 8,022,181 | B2 | 9/2011 | Srivastava |
| 8,063,018 | B2 | 11/2011 | Ni et al. |
| 8,101,379 | B2 | 1/2012 | Wu et al. |
| 8,153,761 | B2 | 4/2012 | Collins et al. |
| 8,206,967 | B2 | 6/2012 | Harrysson et al. |
| 8,252,896 | B2 | 8/2012 | Hsiao et al. |
| 8,314,208 | B2 | 11/2012 | Collins |
| 8,361,965 | B2 | 1/2013 | Fan et al. |
| 8,383,770 | B2 | 2/2013 | Dalton et al. |
| 8,404,724 | B2 | 3/2013 | Sinha et al. |
| 8,415,454 | B2 | 4/2013 | Joshi et al. |
| 2002/0045589 | A1 | 4/2002 | Shen |
| 2004/0229806 | A1 | 11/2004 | Shen |
| 2005/0090651 | A1 | 4/2005 | Smith et al. |
| 2005/0165217 | A1 | 7/2005 | Guinn et al. |
| 2006/0063699 | A1 | 3/2006 | Larsen |
| 2006/0172319 | A1 | 8/2006 | Yan et al. |
| 2006/0276626 | A1 | 12/2006 | Tovi et al. |
| 2007/0042946 | A1 | 2/2007 | Ni et al. |
| 2007/0055048 | A1 | 3/2007 | Cool et al. |
| 2007/0093423 | A1 | 4/2007 | Tovi et al. |
| 2007/0293418 | A1 | 12/2007 | Larsen |
| 2008/0015152 | A1 | 1/2008 | Larsen |
| 2008/0025966 | A1 | 1/2008 | Currie |
| 2008/0051558 | A1 | 2/2008 | Zhou |
| 2008/0139785 | A1 | 6/2008 | Larsen |
| 2008/0227954 | A1 | 9/2008 | Larsen |
| 2008/0234467 | A1 | 9/2008 | Larsen |
| 2008/0253992 | A1 | 10/2008 | DeFrees et al. |
| 2008/0287650 | A1 | 11/2008 | Tovi et al. |
| 2009/0054319 | A1 | 2/2009 | Talley et al. |
| 2009/0062511 | A1 | 3/2009 | Palle et al. |
| 2009/0131636 | A1 | 5/2009 | Bussat et al. |
| 2009/0137779 | A1 | 5/2009 | Ni et al. |
| 2009/0269422 | A1 | 10/2009 | Yu |
| 2010/0029916 | A1 | 2/2010 | Tovi et al. |
| 2010/0056755 | A1 | 3/2010 | Hsiao et al. |
| 2010/0081788 | A1 | 4/2010 | Hsiao et al. |
| 2010/0160604 | A1 | 6/2010 | Dalton et al. |
| 2010/0168443 | A1 | 7/2010 | Geysen |
| 2010/0184952 | A1 | 7/2010 | Takahashi |
| 2010/0273982 | A1 | 10/2010 | Tovi et al. |
| 2010/0292436 | A1 | 11/2010 | Bai et al. |
| 2011/0046063 | A1 | 2/2011 | Palepu et al. |
| 2011/0160431 | A1 | 6/2011 | Tovi et al. |
| 2011/0190475 | A1 | 8/2011 | Nishiuchi et al. |
| 2011/0224150 | A1 | 9/2011 | Yu |
| 2011/0251372 | A1 | 10/2011 | Sommen et al. |
| 2011/0288235 | A1 | 11/2011 | Hsiao et al. |
| 2011/0312878 | A1 | 12/2011 | Larsen |
| 2011/0319594 | A1 | 12/2011 | Bai et al. |
| 2012/0041173 | A1 | 2/2012 | Collins |
| 2012/0135931 | A1 | 5/2012 | Kini et al. |
| 2012/0149868 | A1 | 6/2012 | Kornbeck et al. |
| 2012/0232014 | A1 | 9/2012 | Smith et al. |
| 2013/0034547 | A1 | 2/2013 | Kelly et al. |
| 2013/0196916 | A1 | 8/2013 | Tovi et al. |
| 2013/0196917 | A1 | 8/2013 | Tovi et al. |
| 2013/0196919 | A1 | 8/2013 | Tovi et al. |
| 2014/0088291 | A1 | 3/2014 | Takahashi |
| 2014/0187745 | A1 | 7/2014 | Wen et al. |

FOREIGN PATENT DOCUMENTS

| | | |
|---|---|---|
| CN | 101372512 | 2/2009 |
| CN | 101475631 | 7/2009 |
| CN | 102260323 | 11/2011 |
| CN | 102336813 | 2/2012 |
| CN | 102532274 | 7/2012 |
| CN | 102641506 | 8/2012 |
| CN | 102702325 | 10/2012 |
| CN | 102731624 | 10/2012 |
| CN | 102924575 | 2/2013 |
| EP | 1314745 | 11/2002 |
| EP | 1 314 745 | 5/2003 |
| EP | 1701969 | 10/2007 |
| KR | 20120069288 | 6/2012 |
| WO | 91/02750 | 2/1991 |
| WO | WO 91/02750 A | 7/1991 |
| WO | 93/05065 | 3/1993 |
| WO | 98/50563 | 11/1998 |
| WO | 2007/067979 | 6/2007 |
| WO | 2008/109079 | 9/2008 |
| WO | 2008/155658 | 12/2008 |
| WO | 2010/028122 | 3/2010 |
| WO | 2010/054503 | 5/2010 |
| WO | 2010/117725 | 10/2010 |
| WO | 2011/071799 | 6/2011 |
| WO | 2012/165546 | 12/2012 |
| WO | 2012/174816 | 12/2012 |
| WO | 2013/042129 | 3/2013 |

(56) References Cited

OTHER PUBLICATIONS

International Search Report for PCT/EP2005/011226 dated Dec. 16, 2005.
Lloyd-Williams et al., Solid-Phase Synthesis of Protected Peptide Segments, Solid-Phase Synthesis—A Practical Guide, 2000, pp. 378-381.
Luo, Juan, Bivalirudin, a direct inhibitor drug against thrombin, Zhongguo Yaoxue Zazhi (Beijing, China), vol. 37, No. 10, 2002, pp. 789-790.
Maraganore et al., Design and characterization of hirulogs: a novel class of bivalent peptide inhibitors of thrombin, Biochemistry, vol. 29, No. 30, 1990, pp. 7095-7101.
Wellings et al., Standard Fmoc Protocols, Methods in Enzymology, vol. 289, pp. 44-67.
Okayama et al., *Anticoagulant peptides; synthesis, stability and antithrombin activity of hirudin C-terminal-related peptides and their disulfated analog*, Chemical and Pharmaceutical Bulletin (Tokyo), vol. 44, No. 7, 1996, pp. 1344-1350, XP001207786.
Freund, E. et al "Solid-phase synthesis of a putative heptapeptide intermediate in vancomycin biosynthesis" Chem. Commun., 1999, 2509-2510.
Burgess & Lim: "Resin type can have important effects on solid phase asymmetric alkylation reactions" Chem. Commun., vol. 1997, 1997, pp. 785-786.
Guillier et al.: "Linkers and cleavage strategies in solid-phase organic synthesis and combinatorial chemistry" Chem. Rev., vol. 100, 2000, pp. 2091-2157.

* cited by examiner

METHOD FOR SOLID PHASE PEPTIDE SYNTHESIS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is the US national phase of international application PCT/EP2005/011226 filed 19 Oct. 2005, which designated the U.S. and claims benefit of EP 04024812.2 filed 19 Oct. 2004, the entire contents of each of which are hereby incorporated by reference.

*SEQUENCE LISTING*

*The instant application contains a Sequence Listing which has been submitted electronically in ASCII format and is hereby incorporated by reference in its entirety. Said ASCII copy, created on Apr. 22, 2015, is named LZAS-69-RI_SL.txt and is 22,633 bytes in size.*

The present invention relates to an improved method of solid phase peptide synthesis of the anticoagulant peptide bivalirudin, a so-called 'hirulog'. It further relates to the respective peptide-solid phase conjugate products comprising the still protected peptide bound to the resin.

Thrombin inhibitors are considered as promising antithrombotics: Proteolytic processing by thrombin is pivotal in the control of blood clotting. Hirudin, a potent clinical thrombin peptide inhibitor from the blood-sucking leech Hirudo medicinalis, consists of 65 amino acids.

Shorter peptide analogs of the peptide segment amino acid positions 45-65 of Hirudin, the so-called Hirulogs, have proven effective in treatment of thrombosis, a life-threatening condition.

Okayama et al. (1996, Chem. Pharm. Bull. 44:1344-1350) and Steinmetzer et al. (1999, Eur. J. Biochem. 265:598-605) devise solid phase synthesis of different hirulogs on Wang resin, that is using ester bonding of the C-terminal Fmoc amino acid to a resin that is esterified to a p-benzyloxybenzyl alcohol radical. The Wang resin requires cleavage of the peptide from resin with concentrated trifluoroacetic acid, for which the resin cleavage amounts to concomittant global deprotection of peptide.

Acidolytic cleavage from the Wang resin is applied under strongly acidic conditions and is known to inevitably incur undesirable alkylation of Trp residues as a side reaction, despite the use of scavenging reagents during acidolysis (Giraud et al., 1999, J. Peptide Science 5:457-461). In particular C-terminal Trp is prone to such side reaction (Atherton et al., 1988, Tetrahedron 44:843-857). Alkylation is caused by aromatic carbenium ions generated from the Wang resin linkers phenoxy moiety. —Whilst the Hirulogs do not contain Trp residues, they do comprise in the C-proximal position a Tyr residue. We found and report here for the first time that this Tyr residue is equally prone to erratic alkylation upon cleavage from Wang resin, negatively affecting product purity.

It is the object of the present invention to devise another or improved method of synthesizing the respective Hirulog peptides that lacks the disadvantages of the prior art.

This object is solved by the peptide-resin conjugates and respective method of synthesis devised by the present invention.

According to the present invention, a method is devised for detaching and deprotecting a peptide-solid phase conjugate to yield finally a peptide, preferably a peptide of the formula D-Phe-Pro-Arg-Pro-Gly-Gly-Gly-Gly-Asn-Gly-Asp-Phe-Glu-Glu-Tyr-Leu (*SEQ ID NO: 8*). Said peptide-solid phase conjugate is comprising a 2-chloro-trityl handle of formula I

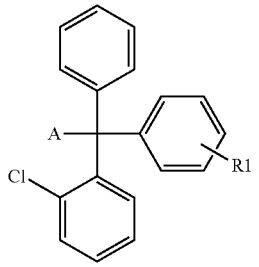

wherein A=Boc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— (*SEQ ID NO: 9*) or A=Fmoc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— (*SEQ ID NO: 10*) or A=$NH_2$-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— (*SEQ ID NO: 11*) and wherein R2, R3, R4, R5, R7, R8, R9 are amino side chain protection groups and wherein R1 is an insoluble solid phase.

The above peptide sequence is that of Hirulog-8 (described in EP-489 070). It is a 20mer bivalent derivative of hirudin (a 65mer), a naturally occurring potent thrombin inhibitor. It is made up from functionally important, linked structural motifs from Hirudin: The active site binding motif D-Phe-Pro-Arg-Pro (*SEQ ID NO: 12*) and the carboxy-terminal sequence $Asn^9$ to $Leu^{20}$ from Hirudin, bridged by a tetraglycine spacer (SEQ ID NO: 1). For sake of definition, herein '-D-Phe-' means D-phenylalanine, as opposed to the naturally occurring L-enantiomer of a given amino acid, in this case Phe.

Optionally, in a further object of the present invention, radical A in formula I may be any of the following:

1. A=P-X1-Tyr(R9)-X2- (*SEQ ID NO: 13*) wherein X1 is a peptidyl moiety, optionally comprising protection groups on individual amino acid side chains, of 0 to 200, preferably 1 to 100, most preferably 2 to 50 amino acids, and wherein X2 is a single, optionally side chain protected, amino acid residue linked to the solid phase via —O— or —NH—, wherein preferably X2 is not Trp, Cys or Arg, and wherein P is either H (i.e. gives α-NH2) or a protection group, preferably the protection group is an orthogonal protection group or is one removable under strongly acidic condition as defined below, more preferably the protection group is selected from the group consisting of Boc, Fmoc, Dde, Nps, Alloc, Z.

2. A=P-X1-Tyr(R9)-Leu-O (*SEQ ID NO: 14*) or is P-X1-Tyr(R9)-X2 (*SEQ ID NO: 13*)

3. A=P-X1-Asp(R4)-Phe-Glu(R5)-Glu(R6)-Ile-Pro-Glu(R7)-Glu(R8)-Tyr(R9)-Leu-O (SEQ ID NO: 2) or is P-X1-Asp(R4)-Phe-Glu(R5)-Glu(R6)-Ile-Pro-Glu(R7)-Glu(R8)-Tyr(R9)-X2 (SEQ ID NO: 3)

4. A=P-X1-[Gly]$_{0-3}$-Asn(R3)-Gly-Asp(R4)-Phe-Glu(R5)-Glu(R6)-Ile-Pro-Glu(R7)-Glu(R8)-Tyr(R9)-Leu-O (SEQ ID NO: 4) or is P-X1-[Gly]$_{0-3}$-Asn(R3)-Gly-Asp(R4)-Phe-Glu(R5)-Glu(R6)-Ile-Pro-Glu(R7)-Glu(R8)-Tyr(R9)-X2 (SEQ ID NO: 5)

5. A=P-X1-Arg(R2)-Pro-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— (SEQ ID NO: 6) or is P-X1-Arg(R2)-Pro-Gly-Gly-Gly-Asn(R3)-Gly-Asp(R4)-Phe-Glu(R5)-Glu(R6)-Ile-Pro-Glu(R7)-Glu(R8)-Tyr(R9)-X2 (SEQ ID NO: 7)

The definitions for P, X1, X2 consistingly apply to all these possible embodiments for A and the resulting peptide-solid phase conjugates.

We found and report here for the first time that said Tyr residue is equally prone to erratic alkylation upon cleavage from Wang resin, negatively affecting product purity. In case of the Hirulog, such modification appears to be promoted by a proximity effect similar to the observations made for Trp by Atherton et al.; however, alkylation of Tyr e.g. in case of Arginine deprotection has been never reported as a general issue, quite in contrast to Trp (Atherton et al., 1989, Solid phase synthesis: A practical approach, IRL press, Oxford). Further, Atherton's observations pertained to C-terminal Trp only, whereas the Tyr residue in the Hirulog peptide, synthesized in the C to N-terminal direction, is only the juxtaproximal, that is the second last residue next to the C-terminus of the growing peptide chain. In hindsight, without wanting to be bound by theory, this may be explained by that phenoxy moieties are more reactive than average arylic compounds in electrophilic substitution. Indeed phenols are used as scavenging agents in acidolytic cleavage from resin (D. S. King et al., 1990, Int. J. Peptid Protein Res., 36, 255). Still then, said side-reaction has not yet been described or suggested by the skilled person, only terminal Trp's having been believed up to now to be vulnerable in this regard. Consequently Wang resin has been widely employed in the prior art, up to recent, for Hirulog synthesis.

The peptide-solid phase conjugate of the present invention can be synthesized by routine solid phase methods well-known in the art, and well described and referenced in Bodanszky et al., Principles of Peptide Synthesis, 2$^{nd}$ ed., Springer Verlag Berlin Heidelberg 1989). Necessarily, due to the acid-lability of the solid phase attachment, such synthetic strategy employs Fmoc chemistry for carrying out the coupling reactions during solid-phase synthesis. Only the last, terminating D-Phe residue may either be Boc- or Fmoc protected. Such Fmoc protection may be eliminated still on-resin, by standard treatment with e.g. 20% piperidine or other Fmoc deprotecting base reagent to yield the peptide-resin conjugate of the present invention but with a free N-terminal amino group. However, such early Fmoc deprotection exposing early on the N-terminus renders would render said free N-terminal D-Phe residue much more prone to undergo racemisation when subjected to detachment from the resin by acidolysis or in particular global deprotection along with detachment under strongly acidic condition. Hence more preferably, the terminating D-Phe residue is Boc-protected or is protected with another protection group that can be easily removed in strongly acid condition, for avoiding the need of a separate Fmoc deprotection step. For the sake of clarity, this includes e.g. Z-(benzyloxy-carbonyl-) protection group, which may be cleaved, inter alia, by strongly acidic conditions as defined in the present context, though hydrogenolytic or HF promoted cleavage is known to be more efficient. Again, a separate Fmoc deprotection step on the terminating D-Phe residue, exposing early on the N-terminus (terminating in free a-amino group, which may be equally denoted as H-D-Phe- . . . or $NH_2$-D-Phe . . . in formula I) and rendering the now free N-terminal D-Phe prone to racemisation e.g. when subjected to global deprotection along with detachment from the resin by acidolysis, is not as good an option though it is another feasible embodiment of the present invention. Said one-step detachment or cleavage along with global deprotection may be carried out in a solvent mixture such as aqueous TFA and DCM, for instance.

In general, according to the present invention, it is possible either to cleave the protected peptide of formula I from the resin concomittant with or, in initial step, to cleave the protected peptide of formula I from the resin preceding the deprotection or global deprotection of amino acid side chains and, preferably, the N-terminal protection group. In the latter embodiment, it is sequentially subjected firstly to weakly acidic condition for cleavage from resin and secondly to strongly acidid condition for cleavage of all remaining protection groups (global deprotection).

Anyway in both conditions, especially the 2-chloro-trityl-resin (CTC resin for short), and e.g. commercially available, closely similar 4-methoxy- or 4-methyl-trityl-resin or to equal or lesser extent the other resins claimed by the present invention, is well suited for avoiding unwanted modification of the juxtaproximal tyrosine residue upon cleavage and/or deprotection. It prevents undesirable alkylation of a juxtaproximal tyrosine, that is a tyrosine that is second last on the C-terminal side, when the tyrosine is concomittantly deprotected upon cleavage from resin. By virtue of the halogeno substituent, optionally the CTC resin allows of effecting resin cleavage of the still protected peptide and tyrosine under very mild acidolytic reaction conditions, e.g. in 0.5% trifluoro acetic acid (TFA) in dichloromethane (DCM), a condition at which most side chain and N-terminal protection groups will normally not be affected and hence alkylation is prevented by segregation of the different deprotection events in time. —In the following, embodiments referred to with regard to CTC resin in particular, as the most preferred embodiment for the solid phase or resin, tacidly refer to the other resins described and claimed in the present invention.

By definition, according to the present invention, a strongly acidic condition as being opposed to a weakly acidic condition means applying at least 50% (v/v) trifluoro acetic acid (TFA) in the solvent. Further, conversely, a protection group requiring strongly acid condition for removal is a protection group that can be removed, at the very least, by 80% TFA. Accordingly, protection groups that require even stronger acids such as HF do not come under the afore mentioned definition in the context of the present invention. A weakly acidic condition is defined by having 0.01% (v/v) to <50% TFA, preferably having 0.1% to 30% TFA.

Either mode, the peptidyl moiety of the present invention notably shows an unexpected absence of undesirable alkylation of the juxtaproximal tyrosine and it is entirely devoid of diketopiperazine side reaction, another possible side reaction that happens upon cleavage from resin and is known to be particular sensitive to the nature of the last two C-terminal amino acids. Without wanting to be limited by theory, it is speculated that a tyrosine at position 2 of the peptide chain next to the CTC resin handle is just at the optimum distance and spacing as to show some stabilising, hydrophobic stacking of the aromatic phenyl moieties, avoiding e.g. the cyclic arrangement that is the prelude to diketopiperazine formation.

Loading of the CTC resin commonly takes place by nucleophilic substitution of the diphenyl-2'-chlorophenyl-chlormethan derivative (hence CTC, short for chloro-trityl-chloride) and is known to be effective. As an option, preloaded Fmoc-amino-acid-CTC resins are commercially available.

Protection groups and their chemistry are further well-known and well-referenced in the art (see Bodanszky, supra). It is needless to say that of course different protection groups R2 to R9 are suited for protection of individual amino acid side chains, different chemical moieties requiring different protection groups. Examples are e.g. histidine being conventionally protectable with trityl or Boc, lysine being protectable with Boc or allyloxycarbonyl, aspartate being protectable as tert.butylester or allylester. Threonine, serine and tyrosine are usually protected as tert-butyl ether. The protection of arginine will be further discussed below. Different modes of deprotection may be applied, e.g. allylic protection groups are laborously removed by Pd-catalyzed reductive acyl-transfer reaction. Z (benzyloxycarbonyl) groups are less expediently employed since requiring hydrogenolysis for efficient removal. Preferably, the protection groups R2 to R9 are acid-labile, 'labile' meaning a cleavage rate of at least 20% of said respective protection group when incubated in DCM solution for up to 5 hours under either weakly or strongly acidic conditions. More preferably according to the present invention, the protection groups R2 to R9 are removed and are only removable under strongly acidic condition as defined above only, that is by way of acidolysis under strongly acidic condition.

R1 is an insoluble, normally polymeric solid phase, e.g. a crosslinked polystyrene/1% divinylbenzol co-polymer. Typically, but not strictly required for working the present invention, such solid phase R1 will of course display further, multiple 2-chloro-trityl-handle moities functionalized with peptide radical A beyond the one shown explicitedly in formula I. More importantly, for being useful in solid-phase synthesis as devised first by Merrifiled, the polymeric solid phase will have a minimum particle size in order to give a true suspension of easily filtratable or pelletable particles of sufficient size, rather than colloidal behaviour. Apart from polystyrene base polymer either directly derivatized with a CTC handle or linker (such as Bayer's 4-carboxytrityl liner, Bayer et al, 13$^{th}$ American Peptide Symposium, Hodges et al., Ed., ESCOM, Leiden, 1994, page 156) or wherein individual benzene moieties of the base polymer have been derivatized to form part of the 2-Chloro-trityl function, further other base polymers such as pure or mixed PEG resins (e.g. Tentagel) or optionally hybrid or grafted resins, wherein e.g. a 2-CTC linker (such as the Bayer linker) has been grafted onto a polystyrene base polymer via a PEG spacer moiety instead of directly reacting the linker with the polystyrene base polymer. Including PEG into a resin provides a more amphilic resin and hence better handling e.g in DCM/TFA mixtures for one-step detachment and deprotection, though loading capacity may then become an issue. —It is to be noted that there are PEG resins which are strictly insoluble of course. However, a technique described by Bayer, et al., Nature 1972, vol. 237, page 512f, described a PEG polymer-borne technique mimicking solid phase separation principle whilst strictly working in solution, the peptide-resin conjugate still being soluble and providing homogenous one phase system. In its preferred meaning in the present context, such resin behaviour is included by the present definition of 'insoluble' since essentially allowing of quick and simple, size-based separation by micro- or ultra-filtration techniques at the microscopic level. In a more preferred meaning, 'insoluble' refers to, in a given solvent system for peptide synthesis, two phase system, one phase being a truly solid, suspended phase.

Preferably, the solid phase has a mesh size of less than 700 mesh (mesh size as defined by the US Bureau of Standards, retrievable e.g. in Römpps Chemie-Lexikon, 7. Auflage, 1973, Franck'sche Verlagshandlung, W. Keller & Co. Stuttgart/Germany).

Preferably, the 2-chloro-trityl-functionalized solid phase of the present invention has a mesh size of from 50 to 600 mesh (as defined by US Bureau of Standards), more preferably of from 60 to 400 mesh, most preferably of from 100 to 300 mesh.

The Tyrosin of the present invention may be protected by different protection groups, e.g. tert.butyl ether or Z- or more preferably 2-Bromo-Z esters. It is equally possible to use tritylalkohol protection groups such as 2-chloro-trityl or 4-methoxy or 4,4' methoxy-trityl groups. Preferably, R9 is a trityl or a tert.butyl protection group. More preferably, R9 is a tertiary butyl (tBu) protection group, meaning the tyrosyl side chain is modified to a tertiary-butyl ether. The tBu group is only efficiently removed under strongly acidic condition.

Preferably, alone and in particular in combination with the further preferred embodiments, the arginine protection group R2 is selected from the group consisting of pentamethyldihydrobenzofuranyl-(Pbf), adamantyloxy-carbonyl and isobornyl-oxy-carbonyl, pentamethylenchromanesulfonyl (Pmc), 4-methoxy-2,3,6-trimethylbenzenesulfonyl (Mtr) and its 4-tert.butyl-2,3,5,6-tetramethyl homologue (Tart) or Boc, which are only cleaved under strongly acidic conditions as defined above. More preferably, R2 is Pbf, Pmc, Mtr, most preferably, it is Pbf; upon global deprotection of side chains under strongly acidic conditions, in usually aqueous medium, bystander-alkylation of deprotected tyrosine is not observed with Pmc, Mtr and esp. Pbf. Pbf's cleavage rate is the highest ever.

Carboxy-protection groups for Glu, Asp are well known, e.g. Mpe, O-1-Adamantyl, O-benzyl and even simply alkyl esters may be used, though less commonly used. For sake of ease, typically and preferably tert.butyl groups are used, independently, for protection groups R4, R5, R6, R7, R8.

Protection group R3 may be of paramount importance because of occurring in above sequence Gly-Asp in Hirulog-8, which dipeptide sequence is particularly prone to aspartimide formation as a side reaction. Aspartimide formation may occur in the protected peptide over each subsequent cycle of coupling during linear synthesis to a minor extent (0.1-0.5%), having cumulative effect in the end. Whilst again protection with a trityl protection group or 2-chloro and 4-methyl or 4-methoxy derivatives thereof, is preferred, likewise adamantyl protection group may be used. Most preferably, a trityl protection group is employed.

It is also to be noted that instead of coupling both side chain and Na protected amino acids, Na-alkyl protected dipeptide modules may be used for coupling during linear synthesis; such dipeptides have secondary structure disrupting effect, easing yield and purity of synthesis. E.g. Fmoc-Gly-(N-Hmb)Gly-OH and Fmoc-Gly-(N-Dmb)Gly-OH are commercially available from EMD Biosciences (Novabiochem). It is to be understood that such N-alkyl groups are not considered protection groups in the sense of the present invention, hence their use or presence is optional and not excluded by the structure of formula I.

In a preferred method of detaching and deprotecting the peptide-conjugate of formula I as essentially set forth in the respective claims, the two step sequential scheme of first conducting an acidolysis under weakly acidic conditions for cleaving the protected peptide from the CTC-resin and secondly removing the remaining protection groups under strongly acidic conditions, is applied.

The reason for this is that a one-step global deprotection of the peptide-solid phase conjugate of formula I suffered from opposing solvent requirements of the fully deprotected product and the hydrophobic, conjugated educt, the need for compromise negatively affecting both product purity and yield. The sequential, stepwise approach eliminates such intrinsic drawbacks, allows of better controlling different reactions and hence allows of optimal yield. According to the present invention, it further enjoys the surprising effect of fully suppressing diketopiperazine formation as a side reaction.

Accordingly, a method is devised of detaching and deprotecting the peptide-solid-phase conjugate of formula I as defined above to give a peptide of formula D-Phe-Pro-Arg-Pro-Gly-Gly-Gly-Gly-Asn-Gly-Asp-Phe-Glu-Glu-Ile-Pro-Glu-Glu-Tyr-Leu (*SEQ ID NO: 15*), characterized in that in a first step, the protected peptide is cleaved from the 2-chloro trityl handle by treatment under weakly acidic condition, preferably with 0.1 to 10% TFA in an polar, aprotic solvent, and that in a second step, the protection groups are removed under strongly acidic condition as defined above.

Preferably, the first step is conducted in a polar, aprotic solvent that is dichloromethane. This is the best solvent to carry out such reaction, in contrast to other solvents such as NMP (N-methylpyrrolidone). It is possible, but not mandatory, to further include a scavenging reagent in the solvent, especially in the solvent system for the second deprotection step, that are present in an amount of 0.1 to 10% (w/w) to the reaction broth for preventing unwanted alkylation of the tyrosine's aromatic core again. Such scavenger intercept reactive alkyl-carbenium ions intermediates that are generated upon removal of the protection groups (which may already happen to a minor extent during cleavage reaction in the first step).

Examples of scavenger is e.g. thioanisol (which also has second, acidolysis-promoting effect—such secondary role and substitutes for aniosol are discussed in Bodanszky M. et al., Int. J. Peptide Protein Res. 23:287). Other examples of scavengers having no such acidolysis effect are phenol and/or trialkylsilanes are used (Stierandova et al., Int. J. Peptide Protein Res. 43, 1994, 31-38).

Preferably, after the first step of cleavage or detachment from resin, the reaction is directly quenched by admixing with pyridine and subsequently recovering the product of step 1 by admixing with water. This way, the product is most simply and efficiently recovered.

In a further embodiment of the present invention, essentially the peptide-solid phase conjugate of formula I is claimed but with the sole difference that the -Arg(R2)-Pro- which is the thrombin cleavage site, is not a standard peptide bond but a chemically modified, pseudoscissile or 'psi' bond (the replacement of an amide bond is indicated by the atoms designated in an extra bracket preceded by the akronym 'psi', see. Rudinger et al., Drug Design Vol. II, Ed. Ariens, E., Academic Press, New York, p. 319 (1971). More preferably, such psi replacement is -Arg[psi$CH_2$NH]Pro- (Kline, T. et al., 1991, Hirulog peptides with scissile bond replacements resistant to thrombin cleavage, Biochem. Biophys. Res. Commun. 177, 1049-1055). Most easily, such psi bond is e.g. introduced during solid-phase synthesis by normal coupling of the growing, conjugated peptide with the premade, Fmoc-protected psi-dipeptide right away.

It is a further object of the present invention, to extend the above described embodiments and methods to peptide-solid phase conjugates comprising a resin moiety other than the above said CTC resin which, still then, similarly allows of cleaving the peptide moiety from the resin under weakly or mildly acidic conditions as defined above. 2-CTC and related trityl and 4-methoxy- and 4-methyl-trityl resins as defined below are still then considered the best embodiment of the present invention, in accordance with the above said.

As a further object, a peptide-resin conjugate of the formula A-W is devised wherein A may be any of the above defined embodiments for A, optionally comprising individual amino acid side chain protection groups and wherein R2 to R9 are defined as above where present, wherein and wherein W is a, preferably insoluble, solid phase or solid phase composite which allows of cleaving the peptide moiety under weakly acidic conditions and which is comprising a resin handle or linker of a. the formula II

II

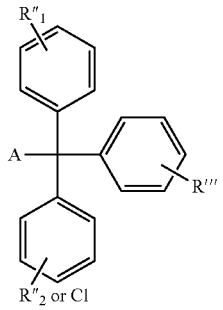

with the proviso that then A where including a residue X2 is always linked via —O— to said handle or linker, and wherein R‴ is the solid phase and wherein R"1, R"2, R"3 are, independently, hydrogen, 4- or 4'-($C_1$-$C_4$ alkyl) or 4- or 4'-($C_1$-$C_4$ alkoxy), and may be the same or different with the proviso that only one of R"1, R"2 may be hydrogen, and wherein R"2 may optionally be 2-Cl with the proviso that then R"1 is H, and wherein more and most preferably, the handle or linker of formula II is selected from the group consisting of 2-chloro-trityl, 4-methoxy-trityl, 4,4'-dimethoxytrityl, 4-methyltrityl, b. or of the formula III

III

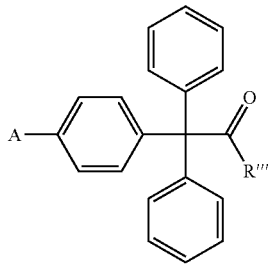

(which may derived from an amino- or hydroxy functionalized resin by acylation with Bayer's 4-carboxytrityl linker, see E. Bayer, supra) with the proviso that then A, also where including a residue X2, is linked via —O— to said handle or linker, R‴ being defined as above, c. or of the formula IV

IV

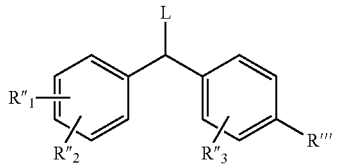

wherein R‴ is a solid phase or polymeric resin, and R"1, R"2, R"3 are, independently, hydrogen, $C_1$-$C_4$ alkyl or $C_1$-$C_4$ alkoxy, and may be the same or different with the provisio that only one of R"1, R"2 may be hydrogen, and wherein L is A (L=A) or wherein L is of formula V

V

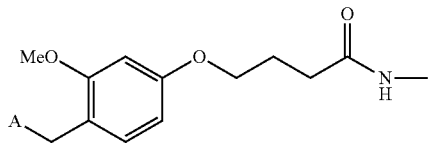

In a further preferred embodiment, the resin handle is of formula VI, the above definitions for radicals R‴, R"1 and R"2 applying,

VI

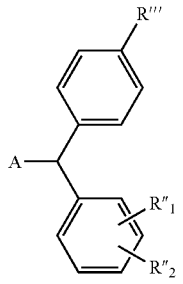

Again even more preferred is that the resin or resin handle is of formula VII, the above definitions for radicals R‴, R"1 and R"2 applying,

VII

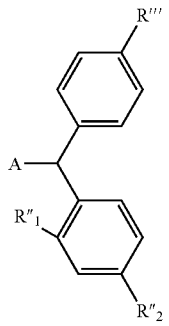

In a further even more preferred embodiment, it is preferred that, where A, optionally including a residue X2, is linked via —O— to said handle or linker of formula VII, R"1, R"2 are independently hydrogen, methyl or methoxy with the provisio that only one of R"1, R"2 may be hydrogen, and that, where A including a residue X2 is linked via —N— to said handle or linker of formula VII, independently are methyl or methoxy, preferably are methoxy. Even more preferably then, A, also where comprising X2, is bound to the handle via a —O— function, R"1 is hydrogen and R"2 is methyl or methoxy and preferably A is a resin or resin handle. Most preferably, R"2 is methyl.

The resin or resin handle composite entity may in principle be any resin employed for synthesis, such as for example a polystyrene-divinylbenzene resin as used by Merrifield along with hydroxybenzyl-phenyl integral linker moieties or by Wang with hydroxy-benzyl-p-benzyloxy moieties, such as for example moieties to which e.g. more acid-labile linkers may be further grafted, or alternatively the latter linkers may be integrally or directly linked to the resin. In principle, a solid phase resin for use in synthesis necessarily comprises at least an integral linker or handle which is part of the solid phase core material; such linker or handle may be considered as an immobilized protection group (Guillier et al., Chem. Rev. 100, 2091-2157, 2000). Examples are e.g. Sieber resin, related xanthenyl type PAL-handle resins, Rink amide resin, Rink acid resin, more complex PEG-grafted polystyrene resins such as tentagel-based Novasyn TG (Novabiochem, Merck Biosciences, Germany) which are available with different grafted handles such as 2'-chloro-trityl, or resins that are constituted by grafting functional handles onto matrix material such as silica gels. Preferably, where the resin is a trityl resin or resin handle, such resin is a 4-methoxy or 4,4'-dimethoxy-trityl resin. Resins as used in the present invention are of standard mesh size, which is about 50-500 mesh, more preferably 100 to 400 mesh. A resin or solid-phase R‴ as shown in formula IV is to be construed as to comprise a crosslinked, polymeric matrix material which may be bound to the handle moiety specified in formulas IV to VII by way of any kind of chemically inert alkyl, alkyloxy, aryloxy or alkylester spacer or linker which is to be considered an integral part of R‴. However, it should be noted that apart from impacting the conditions of cleavage from the resin, the chemical nature of the resin material and in particular the chemical nature of the handle group may well influence synthetic efficiency of coupling and especially lactamisation reactions in a yet poorly understood fashion. The yields of mature peptide at the on-resin stage may differ depending on the type of resin or resin handle employed. For this reason, in an preferred embodiment according to the present invention the resin or resin handle is of formula IV as set forth in the claims in detail, more preferably of formula VI and most preferably of formula VII as set forth in the claims in detail. Examples of such resins or resin handles are (4-methoxyphenyl)-methyl- and (4-methylphenyl)-methyl-polystyrene (Atkinson et al., 2000, J. Org. Chem. 65, 5048), resins in O- or N-linkage to the peptide moiety and their PEG-resin derivatives, respectively. Further examples are e.g. acid-labile HMPB-MBHA o HMPB-BHA resin (Sieber et al., 1987, Tetrahedron Lett. 28, 6147), acid-labile Rink amide resin or Rink acid resin (Rink et al., 1987, Tetrahedron Lett. 28,3787). The term 'acid-labile' refers to essentially quantitative cleavage in 2-10% TFA in dichloromethane at ambient temperature for at least an hour. Surprisingly, using such preferred resins having the diphenyl-methyl structural core motif allow for more efficient coupling reaction during linear synthesis and lactamisation; notably, such resins also allow a lower reaction temperature of 15-25° C. as compared to the standard 40° C. required for efficient coupling on e.g. tritylresins.

EXPERIMENTS

1. Synthesis of Boc-D-Phe-Pro-Arg(Pbf)-Pro-Gly-Gly-Gly-Gly-Asn(Trt)-Gly-Asp(tBu)-Phe-Glu(tBu)-Glu(tBu)-Ile-Pro-Glu(tBu)-Glu(tBu)-Tyr(tBu)-Leu-O-2-CTC (*SEQ ID NO: 16*) ([Protected] *protected* Hirulog-8, Described in EP489 070, Carboxyterminally Conjugated in Ester Linkage to 2-CTC Resin)

All reagents were sourced from EMD Biosciences (Madison, Wis./U.S.A.; Novabiochem-brand). Polystyrene-based 2-C1Trt (CTC) resin (Cbl Patras, Greece), preloaded with Fmoc-Leu-OH, was of 100-200 mesh as regards the base polymer and of 60-200 mesh as regards the preloaded, final CTC resin product. Loading density was about 0.60 mmol/g Individual amino acids were sourced as either Fmoc amino acids or, in case of D-Phe, as readily Boc-protected Boc-D-Phe. Couplings were carried out with TCTU in dichloromethane/N-methylpyrrolidone (NMP), in the presence of Hünig-Base (disopropyl-ethyl-amine, DIEA). Usually, 1.5 eq. of the Fmoc or Boc protected amino acid were used, except for coupling of Fmoc-Arg(Pbf), where 2.5 eq. were used. Similarly, the standard coupling reaction time of 60 min. (at 30° C.) was extended to 90 min. in case of Fmoc-Arg (Pbf). In process control of coupling efficiency was effected by means of the Kaiser test or Chloranil tests.

Fmoc deprotection was carried out with 3-4 cycles of 20% piperidine in NMP at 30° C., with suitable rinsing with NMP in between.

2. Synthesis of Boc-D-Phe-Pro-Arg(Pbf)-Pro-Gly-Gly-Gly-Gly-Asn(Trt)-Gly-Asp(tBu)-Phe-Glu(tBu)-Glu(tBu)-Ile-Pro-Glu(tBu)-Glu(tBu)-Tyr(tBu)-Leu-OH (*SEQ ID NO: 17*)

Cleavage from 48.3 g resin (about 100 ml swollen resin) as generated in experiment 1 above was achieved with 3 cycles of 15 min. each at 15° C., 2% (w/w) TFA, 1% (w/w) triethylsilane (TES) in dichloromethane. The reaction was stirred by nitrogen bubbling; the colour of the reaction changed from cycle to cycle from yellow/orange to brownish. After each cycle, cleavage reaction was directly quenched by pouring the whole reaction broth into dilute pyridin (pyridine/ethanol 1:9 (v/v)). Resin was then removed by filtration with a frit and subjected to the next cycle. All filtrates were pooled, concentrated to an orange semi-liquid under vacuo (RotaVap), washed with DCM, resuspended in 400 ml double distilled water, stirred at room temperature, filtrated, washed with water and dried. Yield was 28.8 g of a slightly yellow powder of analytical quality (~90% pure). Product was analyzed by HPLC and LC-MS.

3. Global Deprotection, Synthesis of $NH_2$-D-Phe-Pro-Arg-Pro-Gly-Gly-Gly-Gly-Asn-Gly-Asp-Phe-Glu-Glu-Ile-Pro-Glu-Glu-Tyr-Leu-OH (*SEQ ID NO: 15*)

Global deprotection was carried out in DCM diluted with cleavage cockatail ('CC'), DCM: 'CC'=1:10 (v/v). 'CC' was made up of TFA/thioanisole/phenol/water/TES in the mixing ratio (% w/w): 89:2.5:2.5:5.0:1.0.1 g of dry product from experiment 2 was dissolved in 10 ml DCM diluted as said above with 'CC' and stirred for 5 hours at room temperature. The product was then recovered by addition of 50 ml methyl-tertbutyl-ether (MTBE, Fluka Chemie, Buchs/Switzerland), cooling the reaction down to 0° C. in a water bath for 30 min. under stirring and filtrating off the salt precipitate that has formed in the whiletime. The filter cake is rinsed with MTBE several times which is then dried at room temperature, yielding 0.8 g of a crude product of about 55% purity as determined by HPLC. The total yield jointly over steps 2 and 3 is about 55%.

4. Comparative Cleavage Experiments and LC-MS Analytics for Synthesis of Hirulog-8 or its C-Terminal Tetrapeptide Fragment Either on Wang Resin or on CTC Resin Using HPLC LC-MS analytics, it could be shown that upon cleavage from resin and global deprotection at strongly acidic conditions, 1-10% of the peptide product proved alkylated in case of Wang resin, whereas no such modification could be observed upon cleavage from CTC resin. MS analysis allowed of mapping that modification to the tyrosyl residue. Synthetic procedure as described above.

SEQUENCE LISTING

```
<160> NUMBER OF SEQ ID NOS: 17

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Gly Gly Gly
1


<210> SEQ ID NO 2
<211> LENGTH: 210
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
0-200 residues
<220> FEATURE:
<223> OTHER INFORMATION: See specification as filed for detailed
description of substitutions and preferred embodiments

<400> SEQUENCE: 2

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Xaa Xaa Xaa
85 90 95

Xaa Xaa Xaa Xaa Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

Xaa Xaa Xaa Xaa Xaa Xaa Xaa Xaa Asp Phe Glu Glu Ile Pro Glu Glu
195 200 205

Tyr Leu
210

<210> SEQ ID NO 3
<211> LENGTH: 210
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
0-200 residues
<220> FEATURE:
<221> NAME/KEY: MOD_RES
<222> LOCATION: (210)..(210)
<223> OTHER INFORMATION: Any amino acid
<220> FEATURE:
<223> OTHER INFORMATION: See specification as filed for detailed
description of substitutions and preferred embodiments

<400> SEQUENCE: 3

```
Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Asp Phe Glu Glu Ile Pro Glu Glu
        195                 200                 205

Tyr Xaa
    210


<210> SEQ ID NO 4
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
      0-200 residues
<220> FEATURE:
<221> NAME/KEY: MOD_RES
<222> LOCATION: (201)..(203)
<223> OTHER INFORMATION: This region may encompass 0-3 'Gly' residues
<220> FEATURE:
<223> OTHER INFORMATION: See specification as filed for detailed
      description of substitutions and preferred embodiments

<400> SEQUENCE: 4

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60
```

```
Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Gly Gly Gly Asn Gly Asp Phe Glu
        195                 200                 205

Glu Ile Pro Glu Glu Tyr Leu
    210                 215


<210> SEQ ID NO 5
<211> LENGTH: 215
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
      0-200 residues
<220> FEATURE:
<221> NAME/KEY: MOD_RES
<222> LOCATION: (201)..(203)
<223> OTHER INFORMATION: This region may encompass 0-3 'Gly' residues
<220> FEATURE:
<221> NAME/KEY: MOD_RES
<222> LOCATION: (215)..(215)
<223> OTHER INFORMATION: Any amino acid
<220> FEATURE:
<223> OTHER INFORMATION: See specification as filed for detailed
      description of substitutions and preferred embodiments

<400> SEQUENCE: 5

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110
```

```
Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Gly Gly Gly Asn Gly Asp Phe Glu
        195                 200                 205

Glu Ile Pro Glu Glu Tyr Xaa
    210                 215


<210> SEQ ID NO 6
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
      0-200 residues
<220> FEATURE:
<223> OTHER INFORMATION: See specification as filed for detailed
      description of substitutions and preferred embodiments

<400> SEQUENCE: 6

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190
```

```
Xaa Xaa Xaa Xaa Xaa Xaa Xaa Xaa Arg Pro Gly Gly Gly Asn Gly Asp
        195                 200                 205

Phe Glu Glu Ile Pro Glu Glu Tyr Leu
    210                 215


<210> SEQ ID NO 7
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
      0-200 residues
<220> FEATURE:
<221> NAME/KEY: MOD_RES
<222> LOCATION: (217)..(217)
<223> OTHER INFORMATION: Any amino acid
<220> FEATURE:
<223> OTHER INFORMATION: See specification as filed for detailed
      description of substitutions and preferred embodiments

<400> SEQUENCE: 7

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Arg Pro Gly Gly Gly Asn Gly Asp
        195                 200                 205

Phe Glu Glu Ile Pro Glu Glu Tyr Xaa
    210                 215


<210> SEQ ID NO 8
<211> LENGTH: 16
<212> TYPE: PRT
<213> ORGANISM: Artificial Sequence
<220> FEATURE:
```

<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: D-amino acid

<400> SEQUENCE: 8

Phe Pro Arg Pro Gly Gly Gly Gly Asn Gly Asp Phe Glu Glu Tyr Leu
1 5 10 15

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Boc
<220> FEATURE:
<221> NAME/KEY: MOD_RES
<222> LOCATION: (1)..(1)
<223> OTHER INFORMATION: D-amino acid

<400> SEQUENCE: 9

Phe Pro Arg Pro Gly Gly Gly Gly Asn Gly Asp Phe Glu Glu Ile Pro
1 5 10 15

Glu Glu Tyr Leu
20

<210> SEQ ID NO 10
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<223> OTHER INFORMATION: N-term Fmoc
<220> FEATURE:
<221> NAME/KEY: MOD_RES
<222> LOCATION: (1)..(1)
<223> OTHER INFORMATION: D-amino acid

<400> SEQUENCE: 10

Phe Pro Arg Pro Gly Gly Gly Gly Asn Gly Asp Phe Glu Glu Ile Pro
1 5 10 15

Glu Glu Tyr Leu
20

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: D-amino acid

<400> SEQUENCE: 11

Phe Pro Arg Pro Gly Gly Gly Gly Asn Gly Asp Phe Glu Glu Ile Pro
1 5 10 15

Glu Glu Tyr Leu
20

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
peptide
<220> FEATURE:
<221> NAME/KEY: MOD_RES
<222> LOCATION: (1)..(1)
<223> OTHER INFORMATION: D-amino acid

<400> SEQUENCE: 12

Phe Pro Arg Pro
1

<210> SEQ ID NO 13
<211> LENGTH: 202
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
0-200 residues
<220> FEATURE:
<221> NAME/KEY: MOD_RES
<222> LOCATION: (202)..(202)
<223> OTHER INFORMATION: Any amino acid
<220> FEATURE:
<223> OTHER INFORMATION: See specification as filed for detailed
description of substitutions and preferred embodiments

<400> SEQUENCE: 13

Xaa Xaa Xaa Xaa Xaa Xaa Xaa Xaa Xaa Xaa Xaa Xaa Xaa Xaa Xaa Xaa
1 5 10 15

Xaa Xaa Xaa Xaa Xaa Xaa Xaa Xaa Xaa Xaa Xaa Xaa Xaa Xaa Xaa Xaa
20 25 30

Xaa Xaa Xaa Xaa Xaa Xaa Xaa Xaa Xaa Xaa Xaa Xaa Xaa Xaa Xaa Xaa
35 40 45

Xaa Xaa Xaa Xaa Xaa Xaa Xaa Xaa Xaa Xaa Xaa Xaa Xaa Xaa Xaa Xaa
50 55 60

Xaa Xaa Xaa Xaa Xaa Xaa Xaa Xaa Xaa Xaa Xaa Xaa Xaa Xaa Xaa Xaa
65 70 75 80

Xaa Xaa Xaa Xaa Xaa Xaa Xaa Xaa Xaa Xaa Xaa Xaa Xaa Xaa Xaa Xaa
85 90 95

Xaa Xaa Xaa Xaa Xaa Xaa Xaa Xaa Xaa Xaa Xaa Xaa Xaa Xaa Xaa Xaa
100 105 110

Xaa Xaa Xaa Xaa Xaa Xaa Xaa Xaa Xaa Xaa Xaa Xaa Xaa Xaa Xaa Xaa
115 120 125

Xaa Xaa Xaa Xaa Xaa Xaa Xaa Xaa Xaa Xaa Xaa Xaa Xaa Xaa Xaa Xaa
130 135 140

Xaa Xaa Xaa Xaa Xaa Xaa Xaa Xaa Xaa Xaa Xaa Xaa Xaa Xaa Xaa Xaa
145 150 155 160

Xaa Xaa Xaa Xaa Xaa Xaa Xaa Xaa Xaa Xaa Xaa Xaa Xaa Xaa Xaa Xaa
165 170 175

Xaa Xaa Xaa Xaa Xaa Xaa Xaa Xaa Xaa Xaa Xaa Xaa Xaa Xaa Xaa Xaa
180 185 190

```
Xaa Xaa Xaa Xaa Xaa Xaa Xaa Xaa Tyr Xaa
        195                 200


<210> SEQ ID NO 14
<211> LENGTH: 202
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H or protection group
<220> FEATURE:
<221> NAME/KEY: MOD_RES
<222> LOCATION: (1)..(200)
<223> OTHER INFORMATION: Any amino acid and this region may encompass
      0-200 residues
<220> FEATURE:
<223> OTHER INFORMATION: See specification as filed for detailed
      description of substitutions and preferred embodiments

<400> SEQUENCE: 14

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Tyr Leu
        195                 200


<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: D-amino acid

<400> SEQUENCE: 15

Phe Pro Arg Pro Gly Gly Gly Gly Asn Gly Asp Phe Glu Glu Ile Pro
```

```
1               5                   10                  15

Glu Glu Tyr Leu
            20


<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Boc
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: Arg(Pbf)
<220> FEATURE:
<221> NAME/KEY: MOD_RES
<222> LOCATION: (9)..(9)
<223> OTHER INFORMATION: Asn(Trt)
<220> FEATURE:
<221> NAME/KEY: MOD_RES
<222> LOCATION: (11)..(11)
<223> OTHER INFORMATION: Asp(tBu)
<220> FEATURE:
<221> NAME/KEY: MOD_RES
<222> LOCATION: (13)..(14)
<223> OTHER INFORMATION: Glu(tBu)
<220> FEATURE:
<221> NAME/KEY: MOD_RES
<222> LOCATION: (17)..(18)
<223> OTHER INFORMATION: Glu(tBu)
<220> FEATURE:
<221> NAME/KEY: MOD_RES
<222> LOCATION: (19)..(19)
<223> OTHER INFORMATION: Tyr(tBu)
<220> FEATURE:
<223> OTHER INFORMATION: C-term O-2-CTC Resin

<400> SEQUENCE: 16

Phe Pro Arg Pro Gly Gly Gly Gly Asn Gly Asp Phe Glu Glu Ile Pro
1               5                   10                  15

Glu Glu Tyr Leu
            20


<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Boc
<220> FEATURE:
<221> NAME/KEY: MOD_RES
<222> LOCATION: (1)..(1)
<223> OTHER INFORMATION: D-amino acid
<220> FEATURE:
<221> NAME/KEY: MOD_RES
<222> LOCATION: (3)..(3)
<223> OTHER INFORMATION: Arg(Pbf)
<220> FEATURE:
<221> NAME/KEY: MOD_RES
<222> LOCATION: (9)..(9)
<223> OTHER INFORMATION: Asn(Trt)
<220> FEATURE:
<221> NAME/KEY: MOD_RES
<222> LOCATION: (11)..(11)
```

-continued

```
<223> OTHER INFORMATION: Asp(tBu)
<220> FEATURE:
<221> NAME/KEY: MOD_RES
<222> LOCATION: (13)..(14)
<223> OTHER INFORMATION: Glu(tBu)
<220> FEATURE:
<221> NAME/KEY: MOD_RES
<222> LOCATION: (17)..(18)
<223> OTHER INFORMATION: Glu(tBu)
<220> FEATURE:
<221> NAME/KEY: MOD_RES
<222> LOCATION: (19)..(19)
<223> OTHER INFORMATION: Tyr(tBu)

<400> SEQUENCE: 17

Phe Pro Arg Pro Gly Gly Gly Gly Asn Gly Asp Phe Glu Glu Ile Pro
1               5                   10                  15

Glu Glu Tyr Leu
            20
```

The invention claimed is:

1. A peptide-resin conjugate A-W, wherein A=P-X1-Asp (R4)-Phe-Glu(R5)-Glu(R6)-Ile-Pro-Glu(R7)-Glu(R8)-Tyr (R9)-X2 (SEQ ID NO:3), wherein X1 is a peptidyl moiety of 0 to 200 amino acids, X1 optionally comprising protection groups on individual amino acid side chains, wherein R9 is an amino side chain protection group and wherein X2 is a single amino acid residue linked to the solid phase via —O— and optionally being side chain or C-terminally protected, and wherein P is H or is a protection group selected from the group consisting of Boc, Fmoc, Dde, Nps, Alloc, Z, and R4, R5, R6, R7 and R8 are amino acid side chain protection groups, and wherein W is a solid phase composite comprising a resin handle or linker a) of the formula II

[

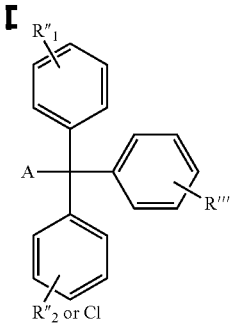

II

]

*II*

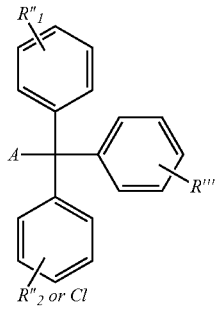

with the proviso that [then] *when* A[, where including] *includes* a residue X2, *A* is [always] linked via —O— to said handle or linker, and wherein R''' is a solid phase, and wherein $R''_1$[,] *and* $R''_2$[, $R''_3$] are[,] independently, H, 4-($C_1$-$C_4$ alkyl) or 4'-($C_1$-$C_4$ alkyl) or 4-($C_1$-$C_4$ alkoxy) or 4'-($C_1$-$C_4$ alkoxy), and [may be] *are* the same or different with the proviso that only one of $R''_1$, $R''_2$ [may] *can* be H, and wherein $R''_2$ may optionally be 2-Cl [with the proviso that then] *when* $R''_1$ is H, b) or of the formula III

[

III

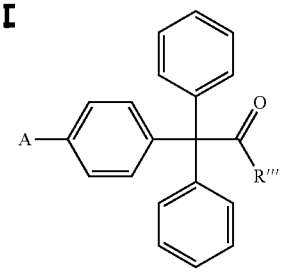

]

*III*

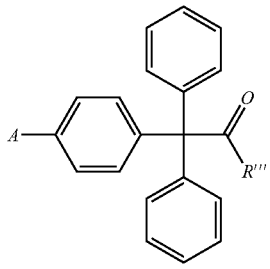

with the proviso that [then] *when* A[, where including] *includes* a residue X2, *A* is linked via —O— to said handle or linker[,] *and* R''' [being defined as above] *is a solid phase*, c) or of the formula IV

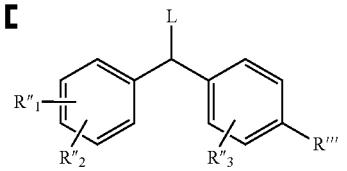

IV

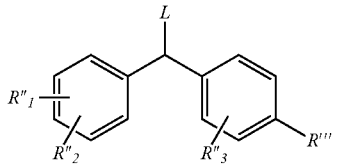

IV wherein R''' is defined as above and $R''_1$, $R''_2$, $R''_3$ are, independently, H, $C_1$-$C_4$ alkyl or $C_1$-$C_4$ alkoxy, and [may be] *are* the same or different with the [provisio] *proviso* that only one of $R''_1$, $R''_2$ [may] *can* be H, and wherein L is A(L=A) or wherein L is of formula V

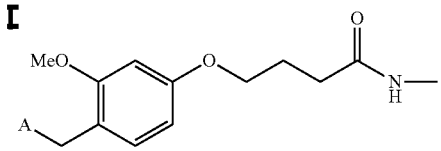

V

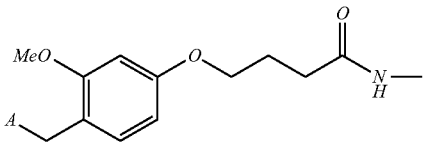

V and wherein W allows of cleaving the peptide moiety under weakly acidic conditions of 0.1% to 30% trifluoroacetic acid.

2. The peptide-resin conjugate of claim 1, [characterized in that] *wherein* W is of formula II as defined or is of formula VI,

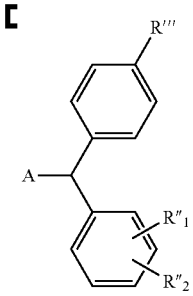

VI

-continued

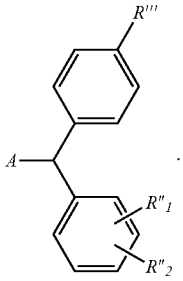

VI

[the above definitions for radicals R''', $R''_1$ and $R''_2$ applying].

3. The peptide-resin conjugate of claim 2, [characterized in that] *wherein* W is of formula VII,

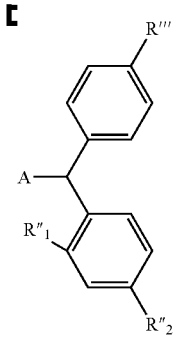

VII

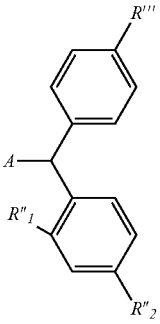

VII

[the above definitions for radicals $R''_1$ and $R''_2$ applying and] *wherein* $R''_1$, $R''_2$ are, independently, H, methyl or methoxy with the [provisio] *proviso* that only one of $R''_1$, $R''_2$ [may] *can* be H, and that, where A including a residue X2 is linked via —N— to said handle or linker of formula VII, independently are methyl or methoxy[, preferably are methoxy].

4. The peptide-resin conjugate of claim 1, wherein the handle or linker of formula II is selected from the group consisting of 2-chloro-trityl, 4-methoxy-trityl, 4,4'-dimethoxytrityl and 4-methyltrityl.

5. The peptide-resin conjugate according to claim 1, [characterized in that] *wherein* X2 is not Trp, Cys or Arg.

6. The peptide-resin conjugate according to claim 1, [characterized in that] *wherein* X1 comprises 0 to 50 amino acid residues.

7. The peptide-resin conjugate according to claim 1, [characterized in that] *wherein* A=P-X1-Asp(R4)-Phe-Glu(R5)-Glu(R6)-Ile-Pro-Glu(R7)-Glu(R8)-Tyr(R9)-Leu-O (SEQ ID NO:2).

8. The peptide-resin conjugate of claim 1, [characterized in that] *wherein* R9 is tertiary-butyl.

9. The peptide-resin conjugate according to claim 1, wherein A=Boc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— or A=Fmoc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— or A=$NH_2$-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— and wherein R2, R3, R4, R5, R6, R7, R8, R9 are amino side chain protection groups and wherein R1 is an insoluble solid phase.

10. The peptide-resin conjugate according to claim 1, [characterized in that] *wherein* the solid phase is polymeric and has a mesh size of less than 700 [(US Bureau of Standards)].

11. The peptide-resin conjugate according to claim 9, [characterized in that] *wherein* R2 is pentamethyldihydrobenzofuranyl, adamantyloxy-carbonyl or isobornyloxy-carbonyl, R9 is tert-butyl or a derivative thereof and that R3 to R8 are acid-labile protection groups.

12. The peptide-resin conjugate according to claim 9, [characterized in that] *wherein* R2 is Pbf and that R4 to R9 are acid-labile protection groups that require at least 50% trifluoroacetic acid for removal.

13. The peptide-resin conjugate according to claim 12, [characterized in that] *wherein* R3 is trityl- and that R4, R5, R6, R7 and R8 are tertiary-butyl.

14. The peptide-resin conjugate according to claim 13, [characterized in that] *wherein* R9 is tertiary-butyl.

15. The peptide-resin conjugate according to claim 1, [characterized in that] *wherein* the -Arg(R2)-Pro- which is the thrombin cleavage site, is -Arg[psi$CH_2$NH]Pro-.

*16. A Hirulog peptide synthesized using the peptide-resin conjugate according to claim 1.*

*17. The Hirulog peptide of claim 16, wherein the Hirulog peptide comprises bivalirudin.*

*18. A process of using a peptide resin conjugate A-W for the synthesis of Bivalirudin, the process comprising*

*cleaving a protected peptide from the peptide resin conjugate A-W,*

*wherein*

*A=Boc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— or*

*A=Fmoc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— or*

*A=$NH_2$-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O—*

*wherein R2, R3, R4, R5, R6, R7, R8, R9 are amino side chain protection groups, and*

*wherein W is a solid phase composite comprising a resin handle or linker*

*a) of the formula II*

*II*

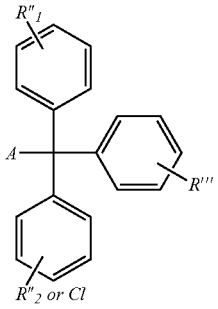

*with the proviso that when A includes a residue X2, A is linked via —O— to said handle or linker,*

*wherein R''' is a solid phase, and wherein $R''_1$ and $R''_2$ are independently, H, 4-($C_1$-$C_4$ alkyl) or 4'-($C_1$-$C_4$ alkyl) or 4-($C_1$-$C_4$ alkoxy) or 4'-($C_1$-$C_4$ alkoxy), and are the same or different with the proviso that only one of $R''_1$, $R''_2$ can be H, and wherein $R''_2$ may optionally be 2-Cl when $R''_1$ is H,*

*b) or of the formula III*

*III*

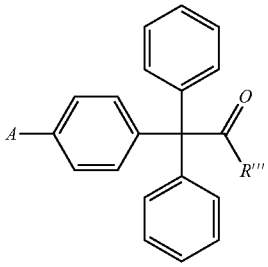

*with the proviso that when A includes a residue X2, A is linked via —O— to said handle or linker and R''' is a solid phase,*

*c) or of the formula IV*

*IV*

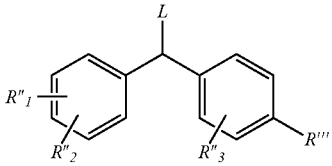

*wherein R''' is defined as above and $R''_1$, $R''_2$, $R''_3$ are, independently, H, $C_1$-$C_4$ alkyl or $C_1$-$C_4$ alkoxy, and are the same or different with the proviso that only one of $R''_1$, $R''_2$ can be H, and* wherein L is A(L=A) or wherein L is of formula V

V

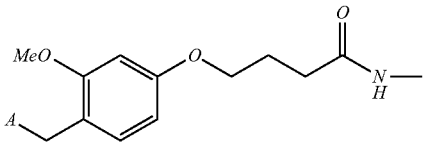

and wherein W allows of cleaving the peptide moiety under weakly acidic conditions of 0.1% to 30% trifluoroacetic acid.

19. The process according to claim 18, further comprising deprotecting the protected peptide to provide a deprotected peptide.

20. The process according to claim 19, wherein the deprotecting is conducted concomitant with cleaving.

21. The process according to claim 19, wherein the deprotecting is conducted after cleaving.

22. The process according to claim 19, wherein the deprotecting is conducted with a composition comprising a strong acid.

23. The process according to claim 19, wherein the deprotecting is conducted with a composition comprising trifluoroacetic acid.

24. The process according to claim 22, wherein the composition further comprises a scavenger.

25. The process according to claim 24, wherein the scavenger comprises thioanisole, phenol, trialkylsilane, or a combination thereof.

26. The process according to claim 18, wherein the cleaving is conducted with a composition comprising a weak acid.

27. The process according to claim 18, wherein the cleaving is conducted with a composition comprising trifluoroacetic acid.

28. The process according to claim 19, further comprising precipitating the deprotected peptide.

29. The process according to claim 19, further comprising contacting the deprotected peptide with methyl-tertbutyl-ether.

30. The process according to claim 18, wherein W is of formula II.

31. The process according to claim 30, wherein formula II is selected from the group consisting of 2-chloro-trityl, 4-methoxy-trityl, 4,4'-dimethoxytrityl and 4-methyltrityl.

32. The process according to claim 18, wherein R9 is tertiary-butyl.

33. The process according to claim 18, wherein R2 is selected from the group consisting of pentamethyldihydrobenzofuranyl, adamantyloxy-carbonyl, isobornyl-oxy-carbonyl, pentamethylenchromanesulfonyl, 4-methoxy-2,3,6-trimethylbenzenesulfonyl and its 4-tert.butyl-2,3,5,6-tetramethyl homologue or Boc.

34. The process according to claim 18, wherein R3 is trityl- and that R4, R5, R6, R7 and R8 are tertiary-butyl.

35. A process of using a peptide resin conjugate A-W for the synthesis of a Hirulog peptide, the process comprising cleaving a protected peptide from the peptide resin conjugate A-W, and deprotecting the protected peptide, wherein A=P-X1-Asp(R4)-Phe-Glu(R5)-Glu(R6)-Ile-Pro-Glu(R7)-Glu(R8)-Tyr(R9)-X2 (SEQ ID NO:3), wherein X1 is a peptidyl moiety of 0 to 200 amino acids, X1 optionally comprising protection groups on individual amino acid side chains, wherein R9 is an amino side chain protection group and wherein X2 is a single amino acid residue linked to the solid phase via —O— and optionally being side chain or C-terminally protected, and wherein P is H or is a protection group selected from the group consisting of Boc, Fmoc, Dde, Nps, Alloc, Z, and R4, R5, R6, R7 and R8 are amino acid side chain protection groups, and wherein W is a solid phase composite comprising a resin handle or linker a) of the formula II

II

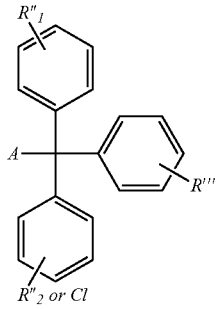

with the proviso that when A includes a residue X2, A is linked via —O— to said handle or linker, wherein R''' is a solid phase, and wherein $R''_1$ and $R''_2$ are independently, H, 4-($C_1$-$C_4$ alkyl) or 4'-($C_1$-$C_4$ alkyl) or 4-($C_1$-$C_4$ alkoxy) or 4'-($C_1$-$C_4$ alkoxy), and are the same or different with the proviso that only one of $R''_1$, $R''_2$ can be H, and wherein $R''_2$ may optionally be 2-Cl when $R''_1$ is H, b) or of the formula III

III

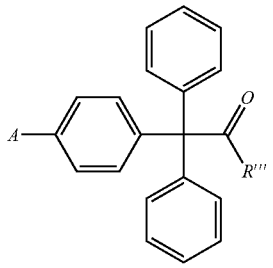

with the proviso that when A includes a residue X2, A is linked via —O— to said handle or linker and R''' is a solid phase, c) or of the formula IV

IV

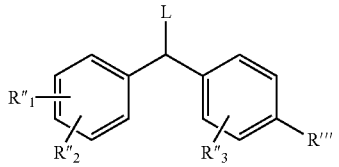

wherein R''' is defined as above and $R''_1$, $R''_2$, $R''_3$ are, independently, H, $C_1$-$C_4$ alkyl or $C_1$-$C_4$

*alkoxy, and are the same or different with the proviso that only one of $R''_1$, $R''_2$ can be H, and*

*wherein L is A(L=A) or wherein L is of formula V*

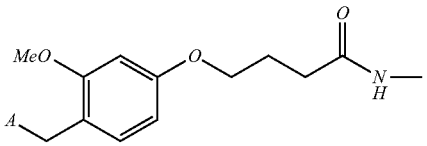

V

*and wherein W allows of cleaving the peptide moiety under weakly acidic conditions of 0.1% to 30% trifluoroacetic acid.*

*36. The process according to claim 35, wherein the deprotecting is conducted concomitant with cleaving.*

*37. The process according to claim 35, wherein the deprotecting is conducted after the cleaving.*

*38. The process according to claim 35, wherein W is of formula II and is selected from the group consisting of 2-chloro-trityl, 4-methoxy-trityl, 4,4'-dimethoxytrityl and 4-methyltrityl.*

*39. The process according to claim 35, wherein X2 is not Trp, Cys or Arg.*

*40. The process according to claim 35 wherein A=P-X1-Asp(R4)-Phe-Glu(R5)-Glu(R6)-Ile-Pro-Glu(R7)-Glu(R8)-Tyr(R9)-Leu-O (SEQ ID NO:2).*

*41. The process according to claim 35, wherein A=Boc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— or A=Fmoc-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— or A=$NH_2$-D-Phe-Pro-Arg(R2)-Pro-Gly-Gly-Gly-Gly-Asn(R3)-Gly-Asp(R4)-Phe-Glu(R5)-Glu(R6)-Ile-Pro-Glu(R7)-Glu(R8)-Tyr(R9)-Leu-O— and wherein R2, R3, R4, R5, R6, R7, R8, R9 are amino side chain protection groups.*

*42. The process according to claim 35, wherein the Hirulog peptide is Bivalirudin.*

* * * * *